United States Patent
Chen et al.

(10) Patent No.: US 10,899,745 B2
(45) Date of Patent: Jan. 26, 2021

(54) PROCESS FOR THE PREPARATION OF 6-(CYCLOPROPANEAMIDO)-4-((2-METHOXY-3-(1-METHYL-1H-1,2,4-TRIAZOL-3-YL)PHENYL)AMINO)-N-(METHYL-D3) PYRIDAZINE-3-CARBOXAMIDE

(71) Applicant: BRISTOL-MYERS SQUIBB COMPANY, Princeton, NJ (US)

(72) Inventors: Ke Chen, East Brunswick, NJ (US); Joerg Deerberg, Columbus, NJ (US); Dong Lin, Monmouth Junction, NJ (US); Michael Dummeldinger, Plainsboro, NJ (US); Bahar Inankur, New Brunswick, NJ (US); Sergei Kolotuchin, Roselle Park, NJ (US); Jun Li, Langhorne, PA (US); Amanda J. Rogers, Asbury, NJ (US); Victor W. Rosso, Monroe Township, NJ (US); Eric M. Simmons, East Brunswick, NJ (US); Daniel S. Treitler, Cranford, NJ (US); Jianji Wang, Dayton, NJ (US); Michael J. Smith, Somerset, NJ (US); Tamas Benkovics, East Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/498,442

(22) PCT Filed: Mar. 29, 2018

(86) PCT No.: PCT/US2018/025100
§ 371 (c)(1),
(2) Date: Sep. 27, 2019

(87) PCT Pub. No.: WO2018/183649
PCT Pub. Date: Oct. 4, 2018

(65) Prior Publication Data
US 2020/0109134 A1 Apr. 9, 2020

Related U.S. Application Data

(60) Provisional application No. 62/478,789, filed on Mar. 30, 2017.

(51) Int. Cl.
*C07D 403/12* (2006.01)
*C07C 211/09* (2006.01)
*C07D 237/24* (2006.01)
*C07D 249/08* (2006.01)

(52) U.S. Cl.
CPC ........... *C07D 403/12* (2013.01); *C07C 211/09* (2013.01); *C07D 237/24* (2013.01); *C07D 249/08* (2013.01); *C07B 2200/13* (2013.01)

(58) Field of Classification Search
CPC .................................................. C07D 403/12
See application file for complete search history.

(56) References Cited

U.S. PATENT DOCUMENTS 9,505,748 B2   11/2016   Moslin et al.

*Primary Examiner* — Emily A Bernhardt
(74) *Attorney, Agent, or Firm* — Bristol-Myers Squibb Company

(57) ABSTRACT

The invention relates to an improved process for synthesizing 6-(cyclopropaneamido)-4-((2-methoxy-3-(1-methyl-1H-1,2,4-triazol-3-yl)phenyl)amino)-N-(methyl-d3) pyridazine-3-carboxamide of the formula: [INSERT CHEMICAL STRUCTURE HERE] Compound I is currently in clinical trials for the treatment of auto-immune and auto-inflammatory diseases such as psoriasis.

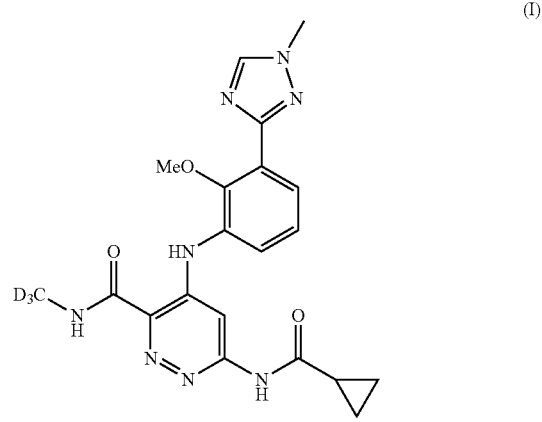

(I)

2 Claims, No Drawings

PROCESS FOR THE PREPARATION OF 6-(CYCLOPROPANEAMIDO)-4-((2-METHOXY-3-(1-METHYL-1H-1,2,4-TRIAZOL-3-YL)PHENYL)AMINO)-N-(METHYL-D3) PYRIDAZINE-3-CARBOXAMIDE

CROSS-REFERENCE TO RELATED APPLICATIONS

This application claims the benefit of U.S. Provisional Application No. 62/478,789, filed Mar. 30, 2017, the disclosure of which is incorporated herein by reference in its entirety.

FIELD OF THE INVENTION

The invention generally relates to a process for the preparation of 6-(cyclopropaneamido)-4-((2-methoxy-3-(1-methyl-1H-1,2,4-triazol-3-yl)phenyl)amino)-N-(methyl-d3) pyridazine-3-carboxamide, a Tyk2 inhibitor currently in clinical trials for the treatment of auto-immune and auto-inflammatory diseases such as psoriasis, as well as novel intermediates used in the process.

BACKGROUND OF THE INVENTION

There is disclosed a process for the preparation of 6-(cyclopropaneamido)-4-((2-methoxy-3-(1-methyl-1H-1,2,4-triazol-3-yl)phenyl)amino)-N-(methyl-d3)pyridazine-3-carboxamide, of formula I:

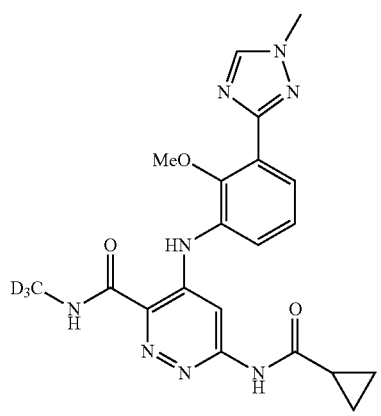

(I)

Compound I, compositions comprising Compound I, and methods of using Compound I are disclosed in U.S. Pat. No. 9,505,748 B2, which is assigned to the present assignee and is incorporated herein by reference in its entirety.

SUMMARY OF THE INVENTION

In a first aspect, the invention provides a process for preparing Compound I of the formula:

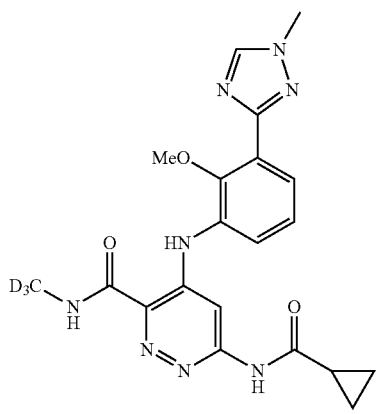

(I)

comprising the steps of a) reacting compound 1a of the formula,

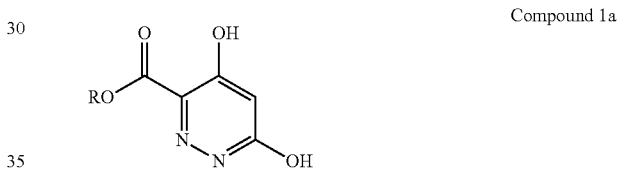

Compound 1a where R is $C_1$-$C_6$ alkyl or aryl;
with activating reagents to afford Compound 2a of the formula,

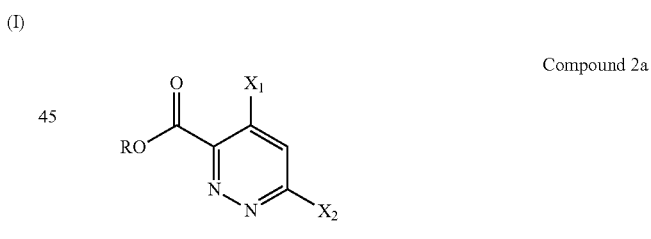

Compound 2a where $X_1$ and $X_2$ are independently halide or sulfonate; and R is defined as above, b) subsequently reacting Compound 2a with an aqueous base to afford Compound 3a of the formula,

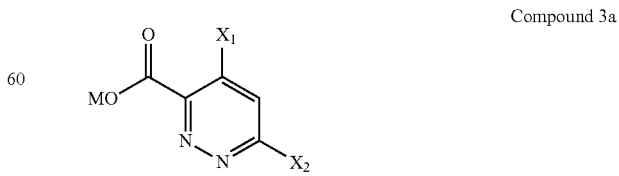

Compound 3a where M is H, Li, Na, K, Cs, Ca, Mg, or Zn, and $X_1$ and $X_2$ are as defined above, c) reacting Compound 3a, with Compound 7 of the formula

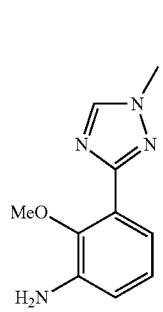

Compound 7 in a suitable solvent, and optionally in the presence of an acid, a base, or metal salts to afford Compound 8a of the formula,

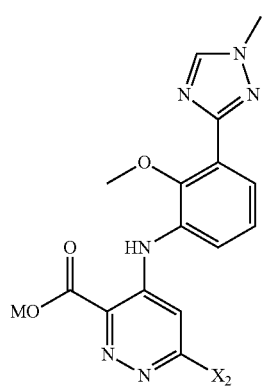

Compound 8a where M and X₂ are defined as above, d) reacting Compound 8a with Compound 10 of the formula

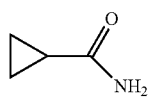

Compound 10 in the presence of a suitable transition metal catalyst, a ligand, one or more bases, and one or more suitable solvents to afford Compound 9a of the formula,

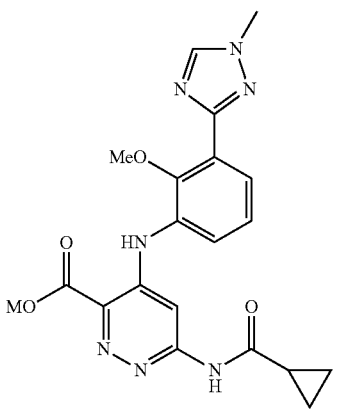

Compound 9a where M is defined as above, e) reacting Compound 9a with Compound 13 (free base or salts thereof) of the formula D₃C—NH₂  Compound 13 in the presence of one or more suitable activators, one or more suitable solvents, and optionally a base, to afford final product Compound I.

In a second aspect, the invention provides a process for preparing Compound I of the formula:

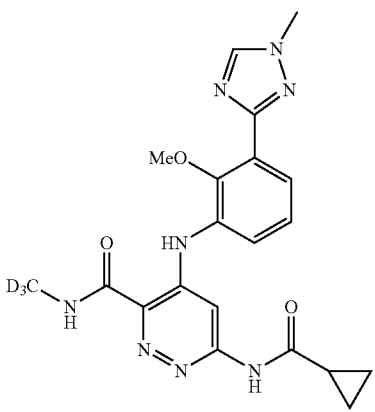

(I)

comprising the steps of a) reacting a compound 1 of the formula

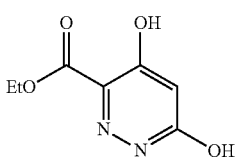

Compound 1 with POCl₃ and optionally an amine base, followed optionally by a buffered aqueous workup to afford Compound 2 of the formula Compound 2

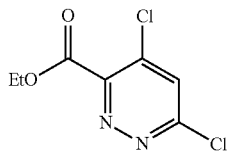

b) subsequently reacting Compound 2 with LiBr and DiPEA in water and acetonitrile to afford Compound 3 of the formula Compound 3

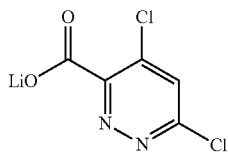

c) reacting Compound 3, with Compound 7 of the formula

Compound 7

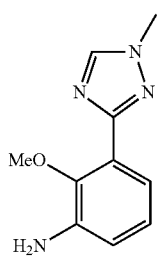

in the presence of zinc acetate in water and 2-propanol, to afford Compound 8 of the formula, Compound 8

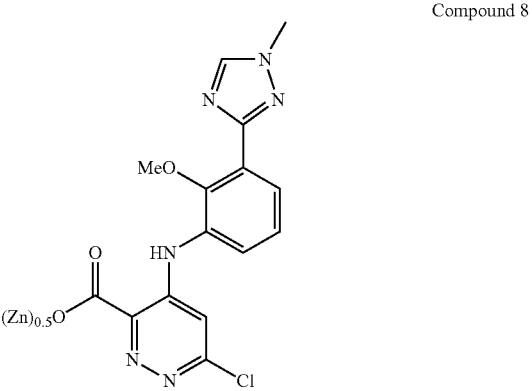

or a hydrate or solvate thereof;

d) reacting Compound 8 with Compound 10 of the formula

Compound 10

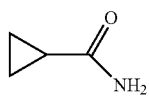

in a palladium catalyzed C—N coupling reaction in the presence of a phosphine ligand, and base, using a dual-base system comprised of potassium carbonate and DBU, followed optionally by isolation from aqueous acetic acid, to afford Compound 9 of the formula Compound 9

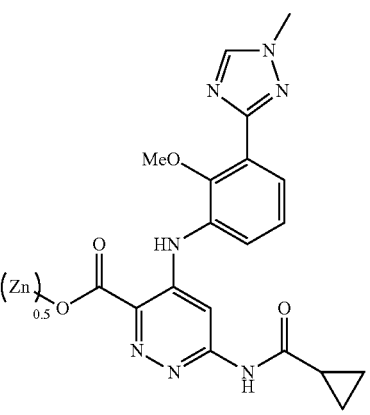

or a hydrate or solvate thereof;

e) reacting Compound 9 with EDC or other coupling agents and Compound 13 of the formula CD₃NH₂HCl     Compound 13

to afford final product Compound I, which may be further purified by crystallization from NMP/IPA.

In a third aspect of the invention, there is provided a process of preparing Compound 7 of the formula

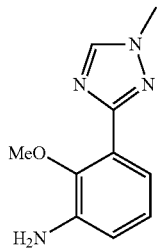

Compound 7 comprising
a) reacting compound 4a of the formula

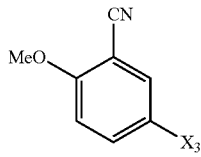

Compound 4a where $X_3$ is Cl, Br, I or F;
with N-methyl-N-formylhydrazine and a suitable base to afford Compound 5a of the formula

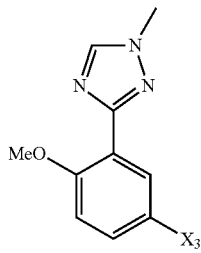

Compound 5a where $X_3$ is defined as above
b) which is then nitrated to afford Compound 6a of the formula

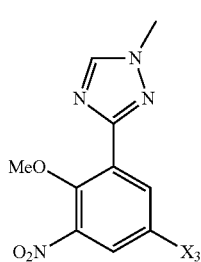

Compound 6a where $X_3$ is defined as above
c) which is subsequently reduced to afford Compound 7.

In a fourth aspect of the invention, there is provided a process of preparing Compound 7 of the formula

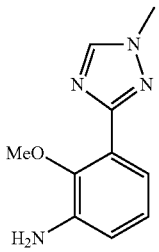

Compound 7 comprising
a) reacting compound 4 of the formula

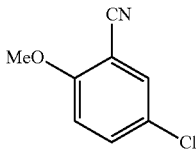

Compound 4 with N-methyl-N-formylhydrazine in the presence of potassium tert-butoxide to afford Compound 5 of the formula

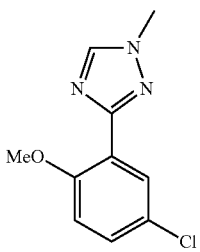

Compound 5 b) which is then reacted with nitric acid in the presence of concentrated sulfuric acid to afford Compound 6 of the formula

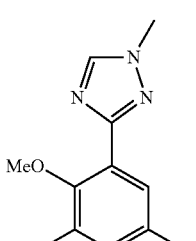

Compound 6 c) which is subsequently reacted with hydrogen gas in the presence of Pd/C, sodium bicarbonate or sodium carbonate and methanol to afford Compound 7.

In a 5th aspect of the invention, there is provided a general process of preparing Compound 13 of the formula $CD_3NH_2$      Compound 13 comprising a) reacting d4-methanol of the formula $CD_3OD$ with activating reagents to afford compound 11a of the formula:

$CD_3X_4$      Compound 11a where $X_4$ is independently halide or sulfonate, b) which is then reacted with sodium diformylamide to afford Compound 12 of the formula Compound 12

$D_3C-N(CHO)_2$ c) which is then hydrolyzed to afford Compound 13 of the formula $CD_3NH_2$      Compound 13

Compound 13 can be isolated as the free base, or as an HCl or HBr salt.

In a 6th aspect of the invention, there is provided a process of preparing Compound 13 of the formula $CD_3NH_2$      Compound 13 comprising a) reacting d4-methanol of the formula $CD_3OD$ with tosyl chloride in the presence of aqueous sodium hydroxide to afford compound 11 of the formula:

$CD_3OTs$      Compound 11 b) which is then reacted with sodium diformylamide to afford Compound 12 of the formula Compound 12

$D_3C-N(CHO)_2$ c) which is then hydrolyzed in the presence of hydrochloride in methanol to afford Compound 13 (as hydrochloride salt) of the formula $CD_3NH_2HCl$      Compound 13.

In a 7th aspect of the invention, there are provided novel intermediates identified above as Compounds 5, 6, 8, 9 and 12.

In an 8th aspect of the invention, there are provided compound 3, 5, 8 and 9 of the formula as its salt or hydrate form. In particular, Compound 3b

[Structure: 4-chloro-6-chloropyridazine-3-carboxylate lithium salt · x H₂O]

Compound 5b or 5c

[Structure: 3-(2-methoxy-5-chlorophenyl)-1-methyl-1,2,4-triazole · x H₂SO₄ or · x HCl]

Compound 8b

[Structure: pyridazine-triazole-methoxyphenyl amine zinc complex (Zn)₀.₅ · x H₂O]

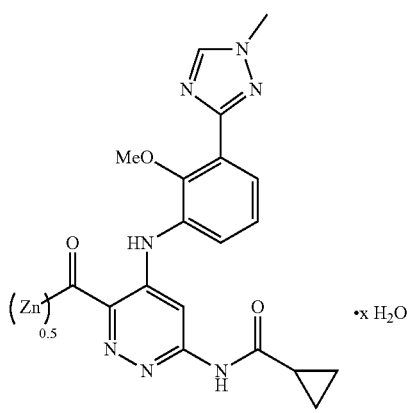

Compound 9b

•x H₂O

Another aspect of the invention provides Compound I prepared by the process of claim 1.

A final aspect of the invention provides a method for treating auto-immune and auto-inflammatory diseases such as psoriasis comprising administering to a mammalian species, preferably a human, in need thereof, a therapeutically effective amount of Compound I, wherein Compound I is prepared utilizing the novel process steps of the invention.

The processes of the invention have several important advantages over prior syntheses of Compound I. In particular, due to the short sequence of chemical steps, high yields and process improvement, the throughput, cycle-time, and overall yield have been dramatically improved. Additionally, the process consistently provides Compound I in high quality for use as a pharmaceutical API.

For the conversion of Compound 8(a) to Compound 9(a), the processes of the first and second aspects are conducted in the presence of a palladium catalyst. Preferred palladium catalysts include, but are not limited to Pd(OAc)$_2$, PdCl$_2$(MeCN)$_2$, Pd$_2$(dba)$_3$, Pd(dba)$_2$, [(Allyl)PdCl]$_2$, [(Crotyl)PdCl]$_2$.

The processes of the first and second aspects are also conducted in the presence of a ligand. Preferred ligands include, but are not limited to phosphine ligands such as SL-J009-1, SL-J009-2, SL-J002-1, SL-J002-2, DPEphos, Xantphos, DPPF, DCyPF, BINAP, or derivatives thereof.

The processes of the first and second aspects are also conducted in the presence of a base. Preferred bases include, but are not limited to, K$_2$CO$_3$, K$_3$PO$_4$, Cs$_2$CO$_3$, DBU, DBN, TMG, or combinations thereof, particularly DBU/K$_2$CO$_3$.

DETAILED DESCRIPTION OF THE INVENTION

The following schemes illustrate the improved synthetic steps of the invention. These Schemes are illustrative and are not meant to limit the possible techniques one skilled in the art may use to manufacture compounds disclosed herein.

As shown below in Scheme 1, the general preparation of compound I is described. Compound 1a is reacted with an activating reagent to give 4,6-diactivatedpyridazine Compound 2a. Ester hydrolysis occurs in the presence of a base to generate compound 3a as carboxylic acid or its salt form. Compound 3a can be selectively substituted at C4 position with compound 7 through contact with an appropriate acid, base or metal salt, or under neutral conditions in the absence of any additives, yielding Compound 8a. Compound 8a can be isolated as its free form, or optionally as a salt with an appropriate base. Compound 8a, in the presence of a metal, an appropriate ligand, and a base, will undergo a coupling process with compound 10 to form Compound 9a. Lastly, the coupling of compound 9a with compound 13 occurs in the presence of an activating reagent and an optional base generates compound I.

Scheme 1

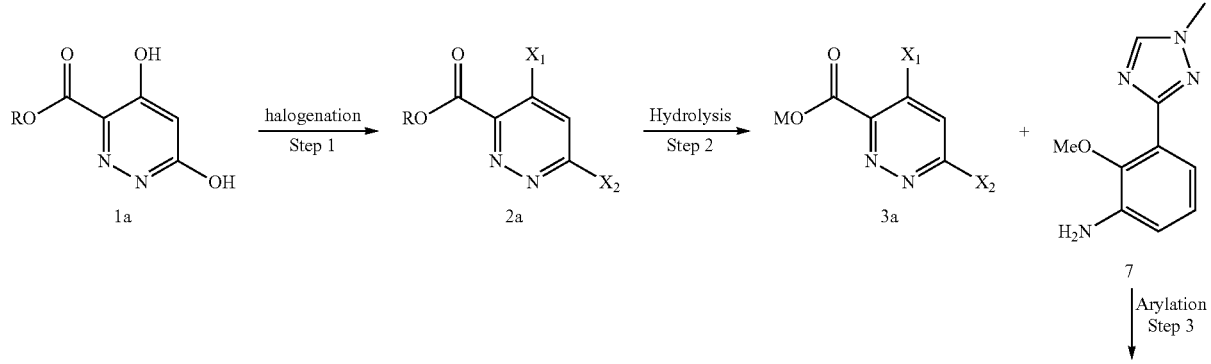

-continued

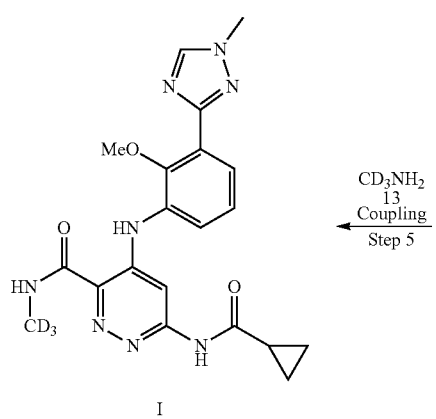
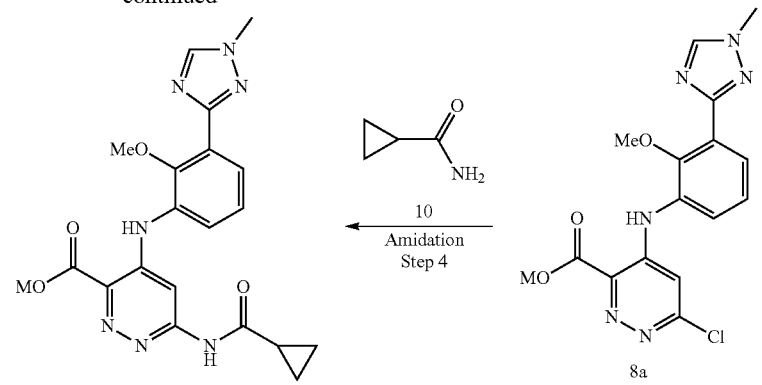

As shown below in Scheme 2, the preparation of Compound I is described. Diethyl 1,3-acetonedicarboxylate is sequentially treated with 4-acetamidobenzenesulfonyl azide and Hunig's base, tributylphosphine and water, and acetic acid, to generate Ethyl 4,6-dihydroxypyridazine-3-carboxylate (Compound 1). Chlorodehydration with phosphorus oxychloride affords the corresponding dichloride (Compound 2), which undergoes hydrolysis in the presence of lithium bromide and Hunig's base in aqueous acetonitrile to yield the lithium carboxylate (Compound 3). Nucleophilic aromatic substitution with compound 7 takes place at C4 position of compound 3, in the presence of zinc acetate, leading to the formation of compound 8 as a zinc salt. Subsequent coupling with compound 10 is catalyzed by palladium acetate and a Josiphos ligand to generate compound 9. Finally, compound 9 undergoes an amidation with compound 13 in the presence of EDC, HOBt and NMI, affording compound I.

Scheme 2

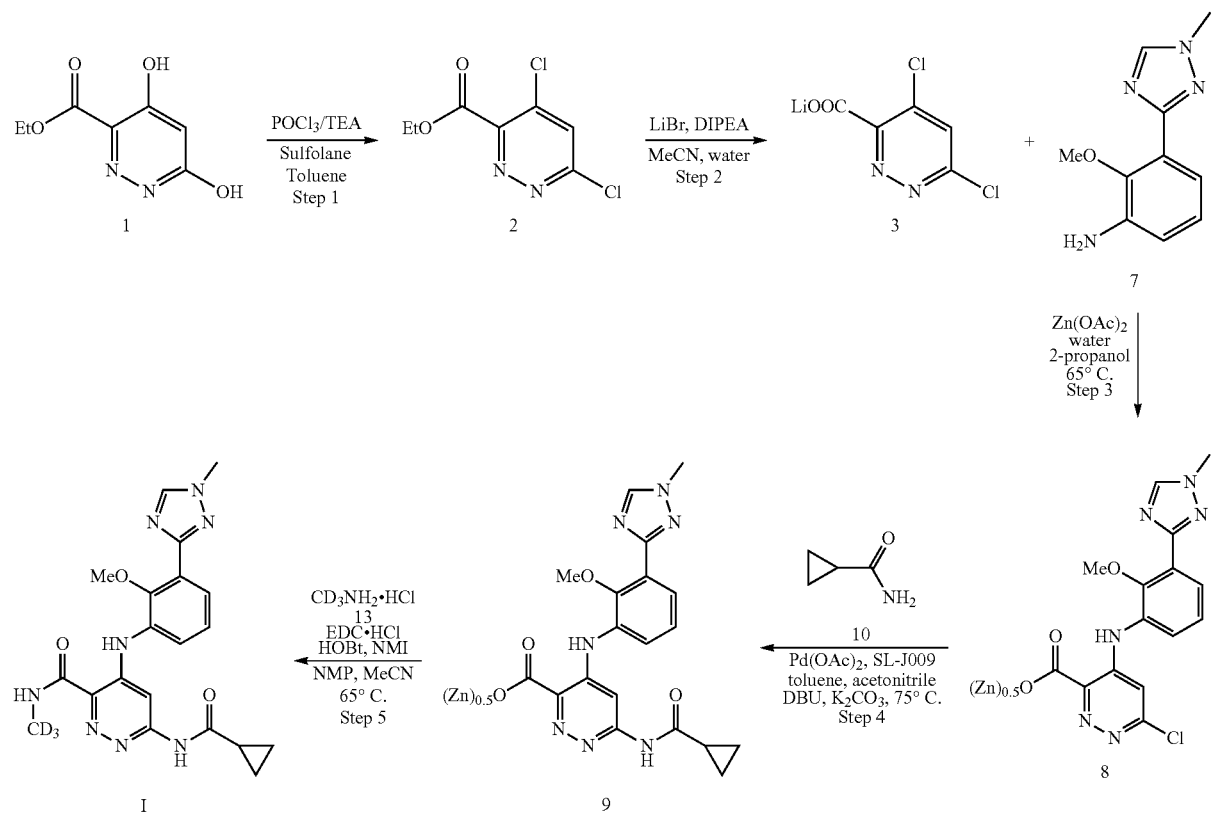

Another process of the invention is disclosed in Scheme 3 shown below. The general preparation of compound 7 is described. A cyclocondensation of compound 4a with N-methyl-N-formylhydrazine affords compound 5a, which undergoes nitration to give compound 6a. Reduction then delivers the corresponding compound 7.

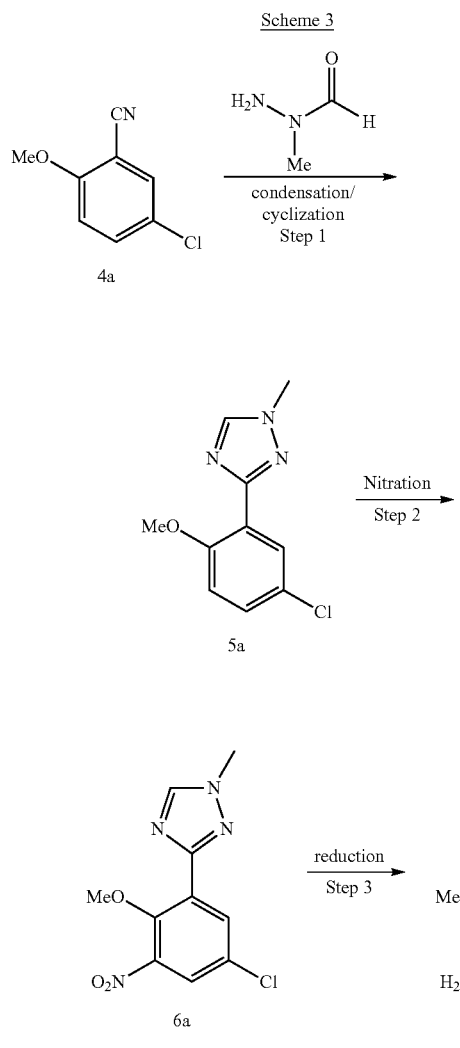

As shown below in Scheme 4, the preparation of Compound 7 is described. Compound 4 reacts with N-methyl-N-formylhydrazine in the presence of potassium tert-butoxide to give compound 5. Treatment of compound 5 with nitric acid and concentrated sulfuric acid delivers compound 6, which reacts with hydrogen gas in the presence of Pd/C and sodium carbonate or sodium bicarbonate to give compound 7.

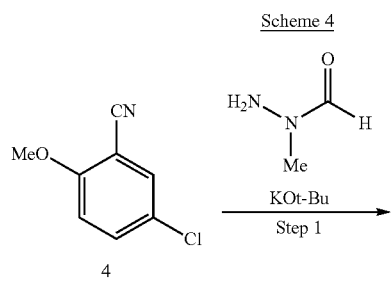

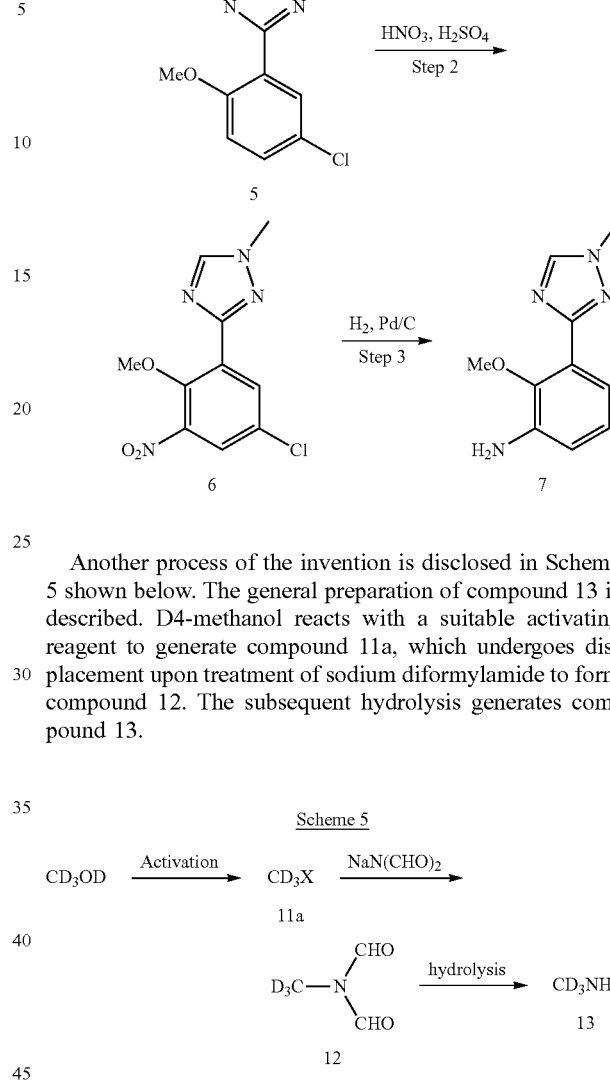

Another process of the invention is disclosed in Scheme 5 shown below. The general preparation of compound 13 is described. D4-methanol reacts with a suitable activating reagent to generate compound 11a, which undergoes displacement upon treatment of sodium diformylamide to form compound 12. The subsequent hydrolysis generates compound 13.

As shown below in Scheme 6, the preparation of Compound 13 is described. D4-methanol reacts with tosyl chloride in the presence of aq sodium hydroxide to give compound 11. Reaction of this compound with sodium diformylamide affords compound 12, which hydrolyzes in the presence of acidic methanol to give compound 13 as it hydrochloride salt.

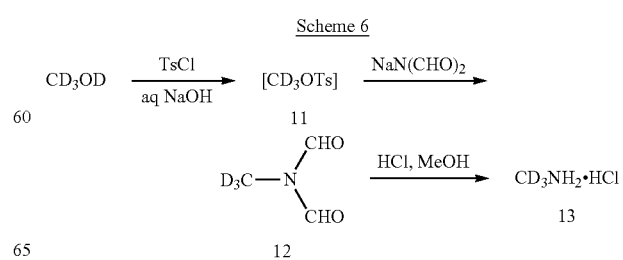

EXAMPLES

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

| Abbreviations | |
|---|---|
| Abbreviation | Name |
| ACN | acetonitrile |
| AcOH | acetic acid |
| AP | area percent |
| aq. | aqueous |
| conc. | concentrated |
| DBU | 1,8-Diazabicyclo[5.4.0]undec-7-ene |
| DIPEA | N,N-diisopropylethylamine (Hunig's base) |
| EDC HCl | 1-(dimethylaminopropyl)-3-ethylcarbodiimide hydrochloride |
| equiv. | Molar Equivalents |
| h | hour(s) |
| HOBt | 1-hydroxy benzotriazole |
| HPLC | high pressure liquid chromatography |
| IPA | Isopropyl alcohol |
| min | minute(s) |
| Me | methyl |
| NaOH | Sodium Hydroxide |
| NMP | n-methylpyrrolidinone |
| NMR | nuclear magnetic resonance |
| Pd/C | palladium on carbon |
| rt/RT | room temperature |
| sat. | saturated |
| t-BuOK | Potassium tert-butoxide |
| THF | Tetrahydrofuran |
| TsCl | p-toluenesulfonyl chloride |

Example 1

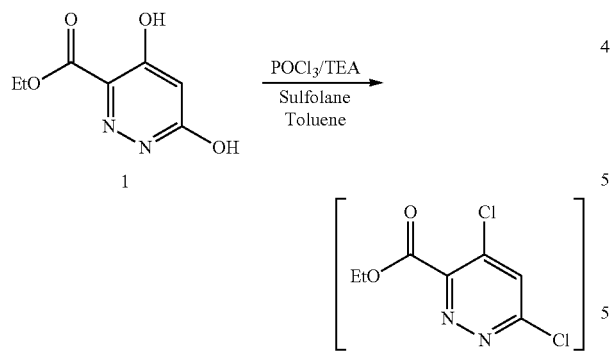

To a glass lined reactor were charged toluene (0.26 Kg), sulfolane (3.4 Kg), compound 1 (1.0 Kg) and POCl₃ (2.7 Kg). The crude was cooled to 0° C. Triethylamine (0.89 Kg) was charged, and the resulting crude mixture was heated to 65° C. and aged till reaction reached completion. The reaction mass was cooled to 5° C.

In a separate reactor, water (7.5 Kg) was charged and cooled to 5° C. The reaction mass was added slowly to the water solution, maintaining the internal temperature below 5° C. Additional water (0.5 Kg) was used to rinse the reactor and aid the transfer. The resulting mixture was agitated at 5° C. for 3 hours, then extracted with MTBE three times (3×4.5 Kg). The combined organic layers were washed sequentially with aq pH 7 buffer solution (5.0 L/Kg, 15 wt % KH₂PO₄/K₂HPO₄) and water (2.5 Kg). The crude was distilled under vacuum until total volume became approximately 3 L/Kg. ACN (2×6.3 Kg) was added followed by additional distillations back to ~3 L/Kg. The crude was cooled to 20° C. to afford Compound 2 as a 30-36 wt % solution in 90-95% yield.

Example 2

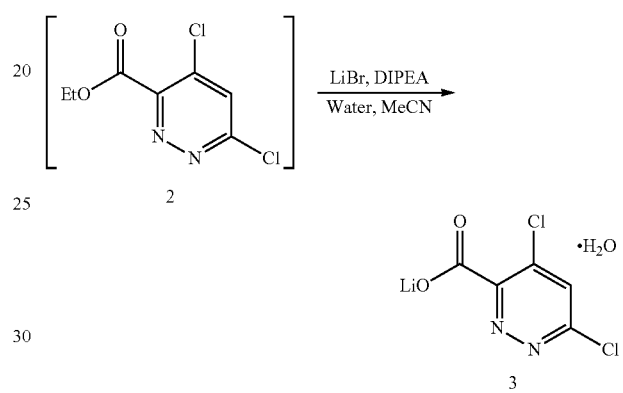

ACN (2.7 Kg), lithium bromide (1.18 Kg) and water (0.65 Kg) were charged to a glass-lined reactor at 25° C. Compound 2 crude solution prepared above (limiting reagent) was added, followed by DIPEA (1.82 Kg). The resulting slurry was agitated at 25° C. until reaction reached completion. The product was isolated by filtration. The crude solid was washed with ACN (1.6 Kg). The cake was dried under vacuum at 45° C. Compound 3 was isolated in 98 AP and 83% yield.

Example 3

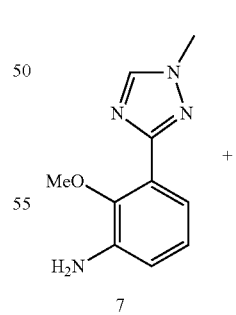

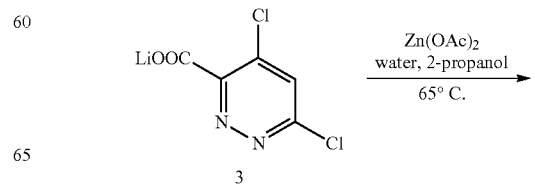

-continued

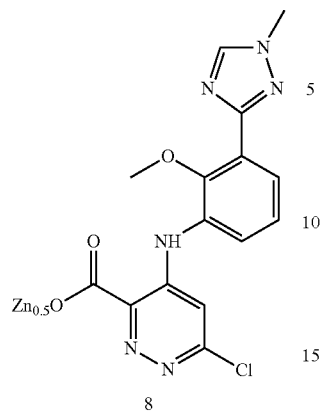

8

Water (6.0 Kg, 6.0 L/Kg) and compound 7 (1.0 Kg) were charged to a glass-lined reactor at 25° C. Zinc acetate dehydrate (1.08 Kg, 1.0 equiv) was added, followed by compound 3 (1.28 Kg, 1.20 equiv). The reactor line was rinsed with 2-propanol (0.79 Kg, 1.0 L/Kg) and water (1.50 Kg, 1.50 L/Kg). The resulting homogeneous solution was heated to 65° C. and aged until reaction reached completion. Water (7.0 Kg, 7.0 L/Kg) was added, and the crude mixture was cooled to 20° C. and aged for 30 min. The product was isolated by filtration. The crude solid was washed sequentially with water (6.0 Kg, 6.0 L/Kg), water (6.0 Kg, 6.0 L/Kg), THF (5.3 Kg, 6.0 L/Kg) and THF (5.3 Kg, 6.0 L/Kg). The cake was dried under vacuum at 70° C. Compound 8 was isolated in 98 AP and 94% yield.

Example 4

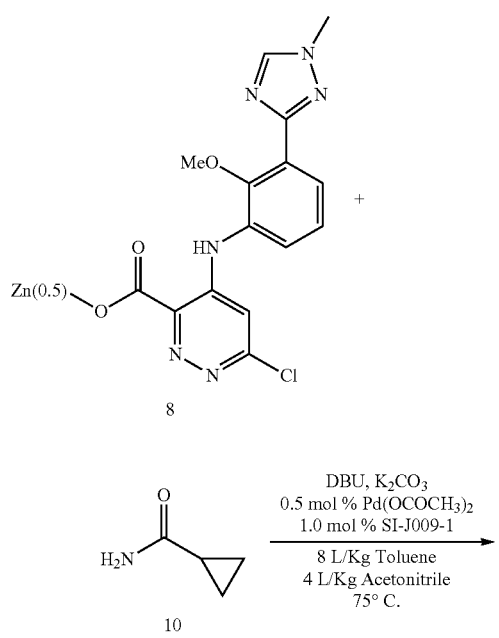

-continued

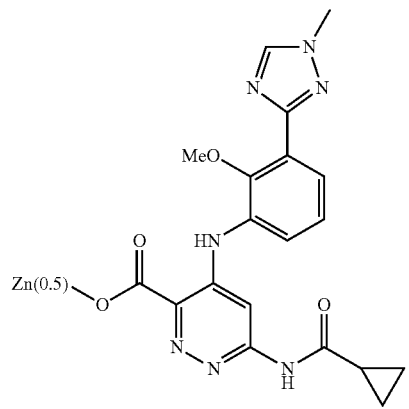

9

A separate glass-lined reactor was flushed with nitrogen. Toluene (0.87 Kg, 1.0 L/Kg) and MeCN (0.79 Kg, 1.0 L/Kg) were charged, followed by (2R)-1-[(1R)-1-[bis(1,1-dimethylethyl) phosphino] ethyl]-2-(dicyclohenxyphosphino) ferrocene (Josiphos SL-009-01) (14.1 g, 1.0 mol %) and palladium acetate (2.9 g, 0.5 mol %). The reactor line was rinsed with toluene (0.43 Kg, 0.5 L/Kg). The resulting pre-formed catalyst solution was kept under nitrogen until further usage.

At 20° C., toluene (3.46 Kg, 4.0 L/Kg) and ACN (1.57 Kg, 2.0 L/Kg) were charged to a glass-lined reactor flushed with nitrogen. Compound 8 (1.00 Kg) was added, followed by DBU (0.39 kg, 1.00 equiv). The reactor line was rinsed with toluene (0.43 Kg, 0.5 L/Kg). Compound 10 (0.54 Kg, 2.5 equiv) and $K_2CO_3$ (325 mesh grade, 0.70 Kg, 2.0 equiv) were added to the reaction mixture, followed by toluene (1.30 Kg, 1.5 L/Kg) and ACN (0.79 Kg, 1.0 L/Kg). The pre-formed catalyst solution was transferred into the reaction mixture, which was then heated to 75° C. and agitated until the reaction reached completion.

The reaction crude was cooled to 20° C. Aq. acetic acid (50 Volume %, 4.0 Kg, 4.0 L/Kg) was charged slowly over the course of 1 h. Glacial acetic acid (10.5 Kg, 10.0 L/Kg) was then added. The resulting homogeneous solution was washed twice with heptane (2×3.42 kg, 2×5.0 L/Kg). The bottom aq. layer was collected and transferred to a clean reactor. Water (5.0 Kg, 5.0 L/Kg) was added, followed by compound 9 seeds (0.01 Kg, 1.0 wt %). The slurry was aged for 2 h at 20° C. Additional water (2.0 Kg, 2.0 L/Kg) was added, and the slurry was further aged for 6 h. The product was isolated by filtration. The crude cake was washed with aq. ACN (50 Volume %, 4.5 Kg, 5.0 L/Kg) followed by ACN (3.9 Kg, 5.0 L/Kg). The cake was dried under vacuum at 65° C. Compound 9 was isolated in 98.5 AP and 84% yield.

Example 5

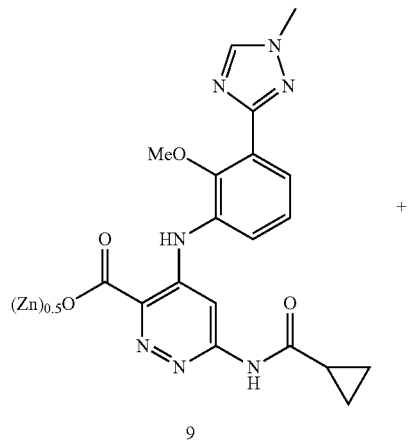

9

EDC·HCl
HOBt, NMI
─────────→
NMP, MeCN
65° C.

CD₃NH₂·HCl
13

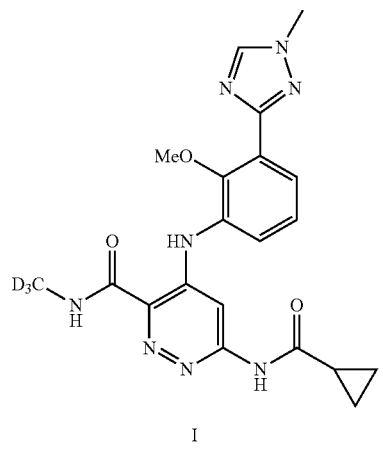

I

NMP (2.06 Kg, 2.0 L/Kg) and ACN (0.78 Kg, 1.0 L/Kg) were charged to a glass-lined reactor and agitated at 20° C. N-Methylimidazole (0.13 Kg, 0.7 eq), Compound 13 (0.17 Kg, 1.2 eq) and Compound 9 (1.00 Kg) were charged to the reaction mixture. The mixture was heated to 65° C. and aged until homogeneous. HOBt 20% wet (0.17 Kg, 0.5 eq), followed by EDC HCl (0.54 Kg, 1.4 eq) were then charged to the reaction mixture. The reactor was rinsed with ACN (0.78 Kg, 1.0 L/Kg), then the resulting mixture was aged at 65° C. until reaction reaches completion. The reaction was quenched by charging water (1.0 Kg, 1 L/Kg), then diluted with ACN (3.0 Kg, 3 L/Kg). The reaction mixture was aged at 65° C. for 1 h, before cooling to 0° C., and aged for an additional 12 h at 0° C. The product was isolated by filtration. The wet cake was washed with 2:1 Water:ACN (2.8 Kg, 3 L/Kg) then ACN (2.4 Kg, 3 L/Kg), before drying under full vacuum at 65° C. Compound I was isolated in >99.5% purity and 91% yield If needed, the product can be subjected to optional recrystallization as follows.

NMP (6.2 kg, 6.0 L/Kg) and Compound I (1.0 Kg) were charged to a glass-lined reactor. The batch was heated to 70° C. to form a pale yellow solution, which was then transferred through a polish filter to a clean vessel at 70° C. 2-Propanol (2.4 kg, 3 L/Kg) was added, followed by Compound I seeds (0.005 Kg, 0.005 Kg/Kg). After aging for 1 h, additional 2-propanol (4.8 kg, 6 L/Kg) was charged over the course of 2 h (3 L/Kg/hr). The slurry was aged for 1 h at 70° C., cooled slowly to 0° C. and aged for additional 12 h at 0° C. Product was isolated by filtration. The wet cake was washed with 2-propanol (2×3.1 kg, 2×4 L/Kg) before drying under full vacuum at 65° C. Compound I was isolated in >99.9% purity and 83% yield.

Example 6

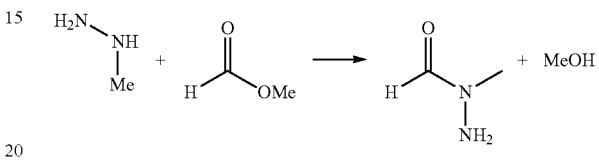

To a glass lined reactor were charged methanol (1.6 Kg/Kg, 2.0 L/Kg) and methyl hydrazine (1 Kg) at 0° C. Methyl formate (0.57 Kg/Kg, 1.1 equiv) was added dropwise. The crude was warmed up to 20° C. and aged for additional 6 h. The crude was distilled under vacuum until total volume became approximately 0.5 L/Kg. Five put/take distillations with 2-MeTHF (5×3.6 Kg/Kg) were undertaken for the purpose of azeotropic drying. The crude was cooled to 20° C. N-Methyl-N-formylhydrazine was isolated as 89-90 wt % solution in 89-91% yield.

Example 7

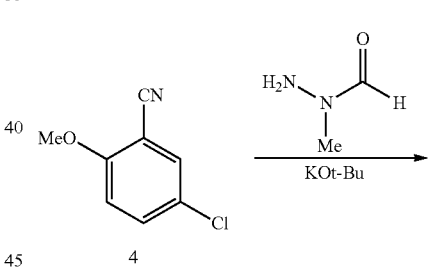

To a glass lined reactor were charged potassium tert-butoxide (1.5 Kg/Kg, 2.4 equiv) and THF (12.2 Kg/Kg) at 0° C. A mixture of compound 4 (1.0 Kg), N-Methyl-N-formylhydrazine (1.0 Kg/Kg, 2.30 equiv) and THF (5.3 Kg/Kg, 6.0 L/Kg) was added slowly. The reactor line was rinsed with THF (0.5 Kg/Kg). The reaction crude was aged at 0° C. until reaction reached completion. Water (5.0 Kg/Kg) was added, and the resulting mixture was aged at 0° C. for 30 min, heated to 40° C. and aged for additional 30 min. The layers were separated and the aq layer discarded.

The organic layer was washed with brine (15 wt %, 5.7 Kg/Kg) before distilling under vacuum until total volume became approximately 5 L/Kg. Four put/take distillations with ethyl acetate (4×10 L/Kg) were undertaken for the purpose of azeotropic drying. The crude was cooled to 20° C. Sulfuric acid (0.66 Kg/Kg, 1.10 equiv) was added, and the slurry was agitated for 2-3 h. Product was isolated by filtration. The cake was consecutively washed with ethyl acetate (2×6.5 L/Kg) and heptane (8 L/Kg), and dried under vacuum at 45° C. Compound 5 was isolated in 99 AP and 83% yield.

Example 8

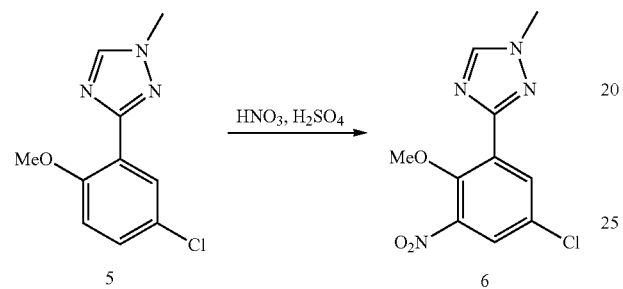

To a glass lined reactor were charged concentrated sulfuric acid (4.5 Kg/Kg) and compound 5 (1.0 Kg) at 0-5° C. Nitric acid (68 wt %, 0.35 Kg/Kg, 1.2 equiv) was added drop-wise. The mixture was agitated at 0-5° C. until reaction reached completion.

In a separate reactor, water (12 Kg/Kg) and methanol (6.5 Kg/Kg, 8.3 L/Kg) were mixed well at 20° C. The nitration crude was transferred slowly into the methanol water mixture. The reactor line was rinsed with methanol (0.5 Kg/Kg). The crude was heated to 40-45° C. Aq. ammonium hydroxide (25 wt %, 7.4 Kg/Kg) was added slowly. The resulting slurry was cooled to 20° C. and agitated for 3 h. Product was isolated by filtration. The cake was washed with water (2×6 L/Kg), and dried under vacuum at 45° C. Compound 6 was isolated in 99 AP and 95% yield.

Example 9

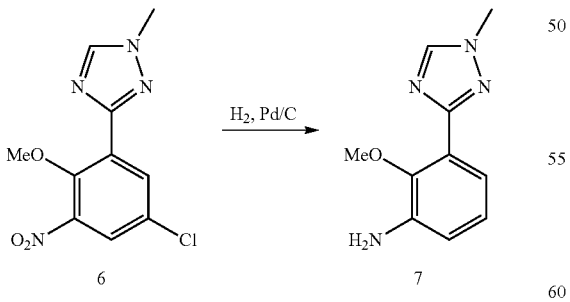

To a high pressure reactor flushed with nitrogen were charged methanol (8.0 Kg/Kg) and compound 6 (1.0 Kg). With careful exclusion of oxygen, sodium bicarbonate (0.6 Kg/Kg, 2.0 equiv) and Pd/C (10% loading, 50% wet, 0.02 Kg/Kg) were added. The reactor was pressurized with hydrogen (41-46 psi), and the reaction mixture was aged at 20° C. for 6 h then heated to 45° C. and aged till reaction reached completion. The reactor was flushed with nitrogen, and the reaction crude was filtered to remove Pd/C. Methanol (5 Kg/Kg) was used to aid the transfer. The combined filtrates were distilled under vacuum until total volume became approximately 2.5 L/Kg. Water (10 Kg/Kg) was added, and the crude was distilled under vacuum until total volume became approximately 2.5 L/Kg. The crude was heated to 70° C. Brine (25 wt %, 9.0 Kg/Kg) was added, and the resulting crude was agitated for 6 h at 70° C. After cooling down to 0° C., the crude was further aged for 6 h. Product was isolated by filtration. The cake was washed with brine (pre-cooled to 0° C., 25 wt %, 2.0 Kg/Kg), and dried under vacuum at 45° C. Compound 7 was isolated in 99 AP and 88% yield.

Example 10

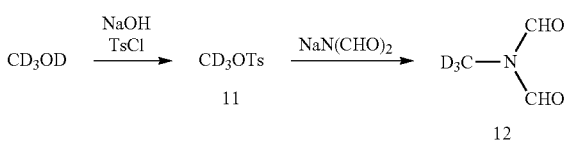

To a glass lined reactor flushed with nitrogen were charged water (16.3 L/Kg) and sodium hydroxide (3.3 Kg, 3.0 equiv). The mixture was aged till sodium hydroxide reached full dissolution. The crude was cooled to 0° C. D4-Methanol (1.0 Kg) and THF (4.5 L/Kg) were charged. A solution of TsCl (6.3 Kg, 1.2 equiv) in THF (6.3 Kg, 7.1 L/Kg) was added over the course of 2 h. The crude was agitated at 0° C. until reaction reached completion. The batch was warmed to 20° C. The layers were separated. The collected organic layer was diluted with MTBE (4.0 Kg, 5.4 L/Kg), washed with brine twice (25 wt %, 4.0 Kg followed by 12 Kg). The organic layer was distilled under vacuum until total volume became approximately 10 L/Kg. Two put/take distillations with ACN (2×10 L/Kg) were undertaken for the purpose of azeotropic drying. The crude was cooled to 20° C. ACN (10.0 Kg, 12.8 L/Kg) and NaN(CHO)$_2$ (3.3 Kg, 1.2 equiv) were added. The crude was heated to 65° C. and agitated until reaction reached completion. After cooling down to 5° C., the mixture was filtered, and the crude cake was washed with ACN twice (2×2.5 Kg, 2×3.2 L/Kg). The combined filtrates were distilled under vacuum until total volume became approximately 3 L/Kg. The crude was cooled to 20° C. Compound 12 was isolated as an oil with 80-85 wt % in 60-70% yield.

Example 11

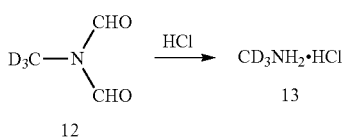

To a glass lined reactor were charged compound 12 (1.0 Kg) and methanol (3.9 Kg, 5.0 L/Kg) at 20° C. A solution of HCl in IPA (5-6 N, 4.5 Kg, 1.5 equiv) was added. The resulting mixture was heated to 50° C. and agitated until reaction reached completion. THF (10 Kg, 11.2 L/Kg) was added slowly and the crude was cooled to 0° C. over 2 h to afford a slurry. The product was isolated by filtration. The cake was washed with THF (3.7 Kg, 4.1 L/Kg), and dried under vacuum at 45° C. Compound 13 was isolated in 80% yield.

If needed, the product can be subjected to optional recrystallization as follows. Methanol (5.6 Kg, 8.3 L/Kg) and Compound 13 (1.0 Kg) were charged to a glass-lined reactor. DBU (0.1 Kg) was added slowly. The crude was agitated for 1 h. THF (12.4 Kg, 13.9 L/Kg) was added slowly, and the resulting slurry was aged for 2 h. The product was isolated by filtration. The cake was washed with THF (2.6 Kg, 2.9 L/Kg), and dried under vacuum at 45° C. Compound 13 was isolated in 60% yield (1st crop). The mother liquor was distilled under vacuum until total volume became approximately 1 L/Kg. Two put/take distillations with methanol (2×2.8 Kg, 2×3.6 L/Kg) were performed and the solution was concentrated back to ~1 L/Kg. The crude was cooled to 20° C. THF (4.8 Kg, 5.4 L/Kg) was added, and the resulting slurry was aged for 2 h. The product was isolated by filtration. The cake was washed with THF (1.0 Kg), and dried under vacuum at 45° C. Compound 13 was isolated in 25% yield (2nd crop).

We claim:

1. A process for the preparation of Compound I of the formula

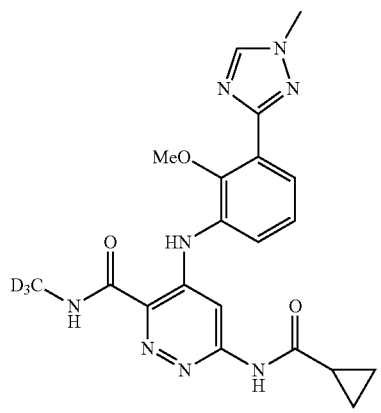
(I)

comprising the steps of a) reacting compound 1a of the formula,

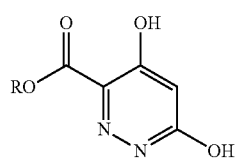
Compound 1a where R is $C_1$-$C_6$ alkyl or aryl;

with activating reagents to afford Compound 2a of the formula,

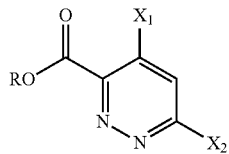
Compound 2a where $X_1$ and $X_2$ are independently halide or sulfonate; and R is defined as above, b) subsequently reacting Compound 2a with an aqueous base to afford Compound 3a of the formula,

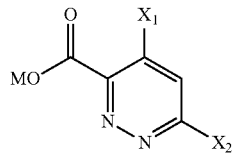
Compound 3a where M is H, Li, Na, K, Cs, Ca, Mg, or Zn, and $X_1$ and $X_2$ are as defined above, c) reacting Compound 3a, with Compound 7 of the formula

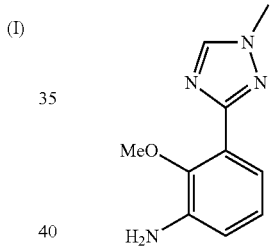
Compound 7 in a suitable solvent, and optionally in the presence of an acid, a base, or metal salts to afford Compound 8a of the formula,

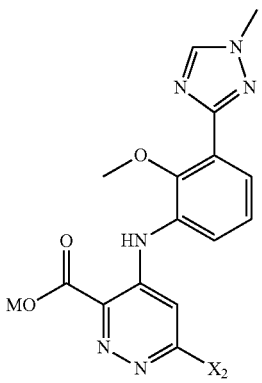
Compound 8a where M and $X_2$ are defined as above, d) reacting Compound 8a with Compound 10 of the formula Compound 10

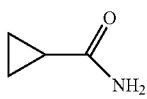

in the presence of a suitable transition metal catalyst, a ligand, one or more bases, and one or more suitable solvents to afford Compound 9a of the formula, Compound 9a

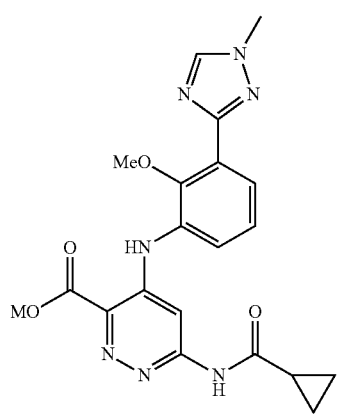

where M is defined as above, e) reacting Compound 9a with Compound 13, or a free base or salt thereof, of the formula, D₃C—NH₂      Compound 13 in the presence of one or more suitable activators, one or more suitable solvents, and optionally a base, to afford Compound I.

2. A process for the preparation of Compound I of the formula (I)

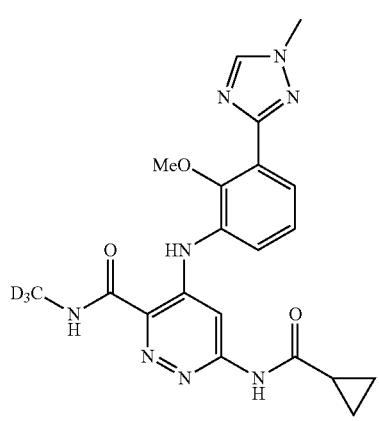

comprising the steps of a) reacting compound 1 of the formula

Compound 1

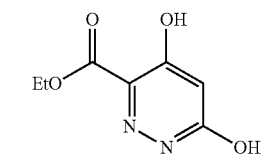

with POCl₃ and optionally an amine base, followed optionally by a buffered aqueous workup to afford Compound 2 of the formula Compound 2

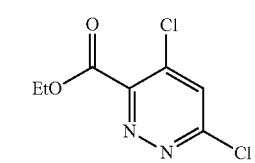

b) subsequently reacting Compound 2 with LiBr and DiPEA in water and acetonitrile to afford Compound 3 of the formula Compound 3

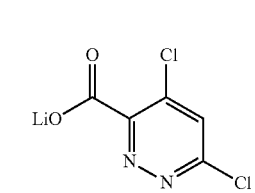

c) reacting Compound 3, with Compound 7 of the formula

Compound 7

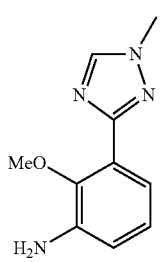

in the presence of zinc acetate in water and 2-propanol, to afford Compound 8 of the formula, Compound 8

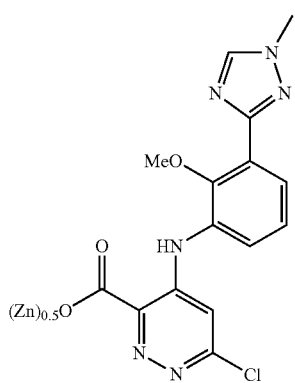

or a hydrate or solvate thereof;
d) reacting Compound 8 with Compound 10 of the formula Compound 10

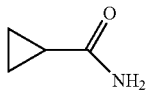

in a palladium catalyzed C—N coupling reaction in the presence of a phosphine ligand, and base, using a dual-base system comprised of potassium carbonate and DBU, followed optionally by isolation from aqueous acetic acid, to afford Compound 9 of the formula Compound 9

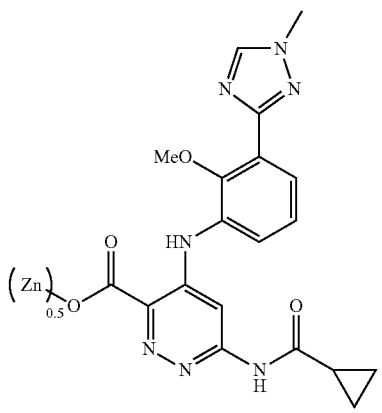

or a hydrate or solvate thereof;
e) reacting Compound 9 with EDC or other coupling agents and Compound 13 of the formula $CD_3NH_2HCl$   Compound 13 to afford Compound I, which may be further purified by crystallization from NMP/IPA.

* * * * *